(12) United States Patent
Fostad Moe

(10) Patent No.: US 11,234,708 B2
(45) Date of Patent: Feb. 1, 2022

(54) TOURNIQUET

(71) Applicant: ARISTEIA AS, Oslo (NO)

(72) Inventor: Gard Fostad Moe, Oslo (NO)

( * ) Notice: Subject to any disclaimer, the term of this patent is extended or adjusted under 35 U.S.C. 154(b) by 237 days.

(21) Appl. No.: 16/333,222

(22) PCT Filed: Sep. 15, 2017

(86) PCT No.: PCT/NO2017/050229
§ 371 (c)(1),
(2) Date: Mar. 13, 2019

(87) PCT Pub. No.: WO2018/052313
PCT Pub. Date: Mar. 22, 2018

(65) Prior Publication Data
US 2019/0247054 A1 Aug. 15, 2019

(30) Foreign Application Priority Data
Sep. 15, 2016 (NO) .................................. 20161471

(51) Int. Cl.
*A61B 17/132* (2006.01)
*A61B 17/00* (2006.01)
*A61B 90/00* (2016.01)

(52) U.S. Cl.
CPC ...... *A61B 17/1327* (2013.01); *A61B 17/1325* (2013.01); *A61B 2017/00477* (2013.01);
(Continued)

(58) Field of Classification Search
CPC . A61B 17/12; A61B 17/1327; A61B 17/1325; A61B 17/132; A61B 17/1322;
(Continued)

(56) References Cited

U.S. PATENT DOCUMENTS 8,652,164 B1   2/2014 Aston
2005/0113866 A1*  5/2005 Heinz ............... A61B 17/1322
                                                   606/203
(Continued)

FOREIGN PATENT DOCUMENTS

EP          2 672 937 A1    12/2013
WO    WO 2012/109524 A1     8/2012
WO    WO-2015196255 A1 * 12/2015 .......... A61M 16/026

OTHER PUBLICATIONS

International Search Report in International Application No. PCT/NO2017/050229, dated May 2, 2018.
(Continued)

*Primary Examiner* — Kathleen S Holwerda
*Assistant Examiner* — Uyen N Vo
(74) *Attorney, Agent, or Firm* — Wallenfelt Law PLC

(57) ABSTRACT

The present invention relates a tourniquet, where tightening of the tourniquet is performed by linear motion by pulling a pull-cord. The tourniquet comprises a tensioning device and a strap. The first end of the strap is coupled to the tensioning device. The second end of the strap is wrapped around a limb and fixed to the tensioning device. The tightening of the tourniquet is achieved by pulling a pull-cord. Linear motion by the pull-cord is translated into winding up the strap inside the tensioning device, and thereby achieving a time-effective tightening of the tourniquet without the need of high forces.

17 Claims, 8 Drawing Sheets

(52) U.S. Cl.
CPC .............. *A61B 2017/00876* (2013.01); *A61B 2090/0807* (2016.02)

(58) Field of Classification Search
CPC .. A61B 2017/12004; A61B 2090/0807; A61B 11/02; A61B 11/006; A61B 11/06; A61B 11/065; A61B 11/08; A61B 11/10; A61B 11/12; A61B 11/125; A61B 11/14; A61B 11/2542; A41F 9/002; A41F 9/025; B60R 2022/1806; B60R 2022/1825
See application file for complete search history.

(56) References Cited

U.S. PATENT DOCUMENTS

| | | | |
|---|---|---|---|
| 2005/0267518 A1* | 12/2005 | Wright ............... | A61B 17/1327 606/203 |
| 2006/0095072 A1* | 5/2006 | TenBrink ........... | A61B 17/1327 606/201 |
| 2010/0137900 A1* | 6/2010 | Chao .................. | A61B 17/1327 606/203 |
| 2012/0204381 A1* | 8/2012 | Ingimundarson ......... | A41F 1/04 24/71.1 |
| 2012/0215254 A1 | 8/2012 | Brub | |
| 2015/0121657 A1 | 5/2015 | Ingimundarson et al. | |
| 2015/0216536 A1* | 8/2015 | Hopman ............ | A61B 17/1322 606/202 |
| 2016/0022277 A1 | 1/2016 | Eikman et al. | |
| 2017/0100131 A1 | 4/2017 | Olbu | |

OTHER PUBLICATIONS

International Preliminary Report on Patentability in International Application No. PCT/NO2017/050229, dated Mar. 19, 2019.

\* cited by examiner

TOURNIQUET

TECHNICAL FIELD OF THE INVENTION

The present invention relates to a tourniquet comprising a strap having a first and a second end for encircling a limb; and a tensioning device comprising a housing wherein the housing comprises at least a first arbor for attaching and winding the first end of the strap; a fastening means for affixing the second end of the strap to the housing; a rotation generating means for providing rotations for the winding in of the strap; a coupling for transferring of rotations from the rotation generating means to the arbor and a locking mechanism to prevent unwinding of the strap.

Said tourniquet is useful for medical and therapeutic treatment of an injured individual.

BACKGROUND OF THE INVENTION

Tourniquets function by constricting the extremity in such a way that the blood flow is occluded. This provides a way for medical personnel and first responders to stabilize the patient in a pre-hospital setting, often at the site of injury. The tourniquet has seen extensive use in modern warfare and has, after the experiences of the U.S. and British military in Afghanistan and Iraq, gained recognition as a life-saving instrument. Tourniquet devices have become part of the personal equipment of U.S. forces and the demanding situations arising in combat means that the equipment must adhere to a number of specifications. Among the top priorities is the safety of use as well as ease of use. The equipment must be readily available and operational to personnel without medical training. Sophisticated equipment is difficult to use in extreme situations such as after terror attacks and in war and there is a need for a tourniquet which is robust in use and easy to handle.

Other considerations include weight and durability. Contrary to surgical tourniquets which utilize pneumatic systems to attain the necessary occlusion pressure, tactical tourniquets are often wholly mechanical in nature due to concerns of durability and reliability. In modern conflict there is an increasing threat from improvised explosive devices and with the added threat from terrorist organizations this has become a concern in urban environments such as major cities as well. If injuries occur due to explosives a tourniquet needs to be available within a convenient range of time and space. Tourniquets used outside a hospital are relevant to the military setting, but also as part of the civilian emergency response such as in accidents and terroristic attacks affecting civilians.

Different types of tourniquets have been developed for use in these cases. There are several disadvantages of many of the known tourniquets such as lack of robustness, lack of possibilities for controlled adjustments of the constriction, afforded power in the constriction, time used for the constriction as well as effectiveness and ease in handling the tourniquet by non-medical and medical persons potentially exposed to extreme situations.

US 2005/0627518 describes a tourniquet with a tensioning mechanism where the tension is adjusted by rotating a worm gear. A disadvantage of this tourniquet is the time taken to achieve occlusion due to a slow adjustment mechanism.

In US2012/0215254A1 a tourniquet is described with a tensioning mechanism with a buckle and pulley assembly. One disadvantage of this tourniquet is a problematic use with one arm.

U.S. Pat. No. 8,652,164B1 describes a tourniquet with a ratchet mechanism for tensioning the tourniquet. A disadvantage of this tourniquet is a cumbersome operation.

US 2011/024719A1 describes a tourniquet with at clamp for tightening the tourniquet. A disadvantage of this tourniquet is a problematic use with one arm.

US2016/0022277A1 describes a tourniquet with pull strap for tightening of the tourniquet. Also this tourniquet is problematic to use with one arm only.

Thus, there is a need for an improved tourniquet which overcomes the above mentioned problems and disadvantages.

OBJECTIVES OF THE INVENTION

The inventor has appreciated that the known tourniquets exhibit one or more problems in operation, for example:
(a) rapid adjustment of the tension to constrict bleeding is difficult,
(b) the tightening mechanism responds slowly to and converts poorly force applied by the operator to tightening of the tourniquet,
(c) pinching of the skin when tightening the tourniquet,
(d) efficiently release of tension when needed to remove the tourniquet,
(e) flexibility in use on limbs with different circumference,
(f) robustness in different operation conditions,
(g) non-intuitive use of the tensioning mechanism,
(h) complex and expensive to manufacture
(i) lack of possibility to release or adjust constriction, and
(j) regulation of maximum constriction to avoid injuries.

The inventor have therefor devised a tourniquet capable of addressing one or more of the problems described in (a) to (j) above.

Thus, an object of the present invention is to provide an improved tourniquet that provides occlusion in an efficient manner, within short time and without the need for high forces during constriction.

Another object of the invention is to provide a tourniquet that may be operated by one hand only.

Yet another object of the invention is to provide a tourniquet that may be operated by two hands, providing more force available for efficient occlusion.

Yet another object of the invention is to provide a tourniquet that may be operated by one or two hands and where the operator can push against the limb for more efficient occlusion.

Yet another object of the invention is to provide a tourniquet that is fool proof and easy to operate, providing the required occlusion within seconds of time.

Yet another object of the invention is to provide a tourniquet that is flexible in use, providing possibility to encircle limbs with different diameter.

Yet another object of the invention is to provide a tourniquet that is robust, providing fewer exposed parts.

Yet another object of the invention is to provide a tourniquet that is safe to use, limiting the damages to the limb where the tourniquet is applied.

Yet another object of the invention is to provide a tourniquet that is more efficient and less expensive to manufacture.

Yet another object of the invention is to provide a tourniquet that is small and lightweight.

Yet another object of the invention is to provide a tourniquet which is easy to release and/or adjust in constriction.

Yet another object of the present invention is to provide a tourniquet allowing to be used in situations with limited space or access to the injured person.

SUMMARY OF THE INVENTION

The objects and advantages are achieved by a tourniquet as defined in the independent claims. Preferred embodiments are also defined in the dependent claims.

According to the present invention, it is provided a tourniquet comprising: a strap having a first and a second end for encircling a limb, and a tensioning device comprising a housing wherein the housing comprises:
at least a first arbor for attaching and winding up the first end of the strap,
a fastening means for affixing the second end of the strap to the housing,
a rotation generating means for providing rotations for winding in the strap,
a coupling for transferring of rotations from the rotation generating means to the arbor, and a locking mechanism to prevent unwinding of the strap. The rotation generating means of the tourniquet comprises a pull-cord for providing rotations for winding in the strap on the arbor. A main advantage of this tourniquet is the possibility of a fast linear constriction of the strap within short time. The pull-cord can be operated by one hand and can be drawn in different directions without affecting the constriction.

Attaching the first end of the strap to the arbor comprises both a solution where the first end is directly attached to the arbor. It may also include a solution with an adjustable attachment for securing the strap to the arbor at a distance from the free end of the first end of said strap. This can for example be done by passing the strap through an opening in the arbor where the arbor has a braking mechanism preventing reverse movement of the strap. This allows pre-tensioning the tourniquet by hand before constriction via the rotation generating means.

Fastening means for affixing the second end of the strap to the housing typically include locks, belts, buckles and similar being suitable for and having the purpose to fasten the second end of the strap to the housing. The fastening means is advantageous in providing a solution for rapid affixing when wrapping the strap around a limb before tightening the tourniquet. The fastening means may also be used as a rapid way to release the tourniquet by detaching the second end from the housing.

By rotation generating means it is also meant a swivel, a wheel, an electrical motor or other suitable means for outputting rotations.

By coupling it is also understood to mean a coupling that transfers rotations from the rotation generating means to the arbor. The coupling may be wheels, gears, belts, sprocket wheels, friction belts, hydraulic fluid transmissions, clutch mechanisms and the like. The coupling is advantageous in that it provides the possibility to increase or decrease the gear ratio, thereby allowing an improved transmission of force impact. Furthermore, it makes it possible to have a distance between the generation means for rotations and the arbor, also allowing the rotation generating means and the arbor to be arranged non parallel.

It is preferred that the rotation generating means comprises a pull cord reel, preferably including a mechanism for recoiling the pull-cord on the reel. The advantage of the recoil reel is that the pull cord can be pulled repeatedly.

It is further preferred that the locking mechanism is releasable for unwinding the first end of the strap. This makes it possible to remove the tourniquet, adjust the tension and to easily check whether the tourniquet is still needed to stop bleeding.

Preferably, the coupling comprises a gear system for transmission of rotations from the reel to at least the first arbor. This has the great advantage that the force needed to constrict the tourniquet can be sufficiently lower. Many of the known tourniquets afford a high degree of force to be constricted and to stop the blood circulation. Using a gear system overcomes this problem. In a particular preferred embodiment, the gear ratio between the reel and the arbor is at least 2:1, more preferably at least 3:1. This will reduce the required force significantly.

The tension device can comprise a release system suitable for disengaging the pull cord reel from at least the first arbor. This would allow the pull cord to be rewinded on to the reel without rotating the arbor.

In another preferred embodiment the fastening means comprises a second arbor for winding up the second end of the strap whereby the second arbor is connected via an additional coupling to the rotation generation means. One advantage of two arbors is that the speed for tightening of the tourniquet is improved.

Preferably, the locking mechanism is configured to unlock above a certain level of the tension applied to the limb. This has the great advantage that damages due to a too high constriction of the strap around the limb may be avoided. Thereby a fast constriction is possible without damaging the limb due to high forces used during the constriction process.

It is also preferred that the strap is made of a smart textile for indicating tension applied to the limb. This has the advantage that the degree of constriction can be signalized to the user when the tourniquet is constricted around a limb and during the constriction process.

In another preferred embodiment of the tourniquet, the tourniquet comprises a release mechanism for preventing the tourniquet being tensioned above a certain tensioning degree, preferably no more than 600 mm Hg. This is advantageous in avoiding damaging the skin or tissue being constricted.

Preferably, the rotation of the arbor is controlled by a spring loaded ball lock mechanism. An advantage of a spring loaded ball lock mechanism is rapid release and locking for adjusting of the occlusion provided by the tourniquet.

In yet another preferred embodiment of the tourniquet, a rotation axis of the at least one arbor is perpendicular to a rotation axis of the pull cord reel. One advantage of this is allowing a larger pull cord reel without increasing the height of the housing.

In yet another embodiment of the tourniquet, the arbor comprises an opening for passing a free end of the first end of the strap through the opening, preferably the opening is provided longitudinally in the arbor. This is advantageous in allowing rapid initial tensioning of the tourniquet.

In another aspect, the tourniquet of the present invention is used in a medical treatment. The tourniquet can be used to control and stop venous and arterial blood circulation to an extremity for a period of time. The strap of said tourniquet is preferably arranged around a limb/extremity and thereafter constricted by pulling the pull cord to wind up the strap on the arbor.

In the disclosed tourniquets according to the present invention, the translation ratio from the reel to the arbor via the gear system is chosen such that one rotation of the reel results in one or more rotations of the arbor, preferably a ratio of 1:3. This is preferred in cases, where it would be advantageous to provide more rapid tightening of the tourniquet. In particular preferred embodiments of the tourniquet the translation ratio is chosen such that one rotation of the reel results in less than one rotation of the arbor, preferably a ratio of 2:1 or 3:1. The advantage of this ratio is that less pull force is needed for tightening of the tourniquet.

The length of the pull-cord in the disclosed tourniquets according to the present invention is typically chosen in such a way that it can easily be operated single handed e.g. if the user is the injured person himself/herself. The pull-cord can typically have a length of 20 cm to 60 cm to be pulled using only one arm. The pull-cord may be shorter than 20 cm to allow a smaller dimension of the pull-cord reel. The pull-cord may be longer than 60 cm to allow an operator to apply more force to the arbor in a single movement. The pull cord handle may be configured for operation by one hand and/or two hands. In circumstances where there is not sufficient space for the full length of the pull cord to be pulled, this can be compensated by pulling the pull cord multiple times to attain the same constriction as pulling the full length of the pull cord.

The strap to be placed around a limb is typically fabricated from a lightweight and strong material, such as polyester or nylon webbing, with a typical width of 3 cm to 10 cm, and more preferably 5 cm wide. Other material may also be employed, such as strong or reinforced synthetic fibers, textiles (woven or non-woven), leather, and cloth. In the context of the invention strong material should be interpreted as a material that is suitable to sustain the tension needed to constrict bleeding from a wound.

The strap may also be wholly or partly be made from a smart textile as described in more detail in the following sections.

DESCRIPTION OF THE DIAGRAMS

Exemplary embodiments of the invention will now be described, by way of example only, referring to the following diagrams in which.

DETAILED DESCRIPTION OF EMBODIMENTS OF THE INVENTION

Figure 1:
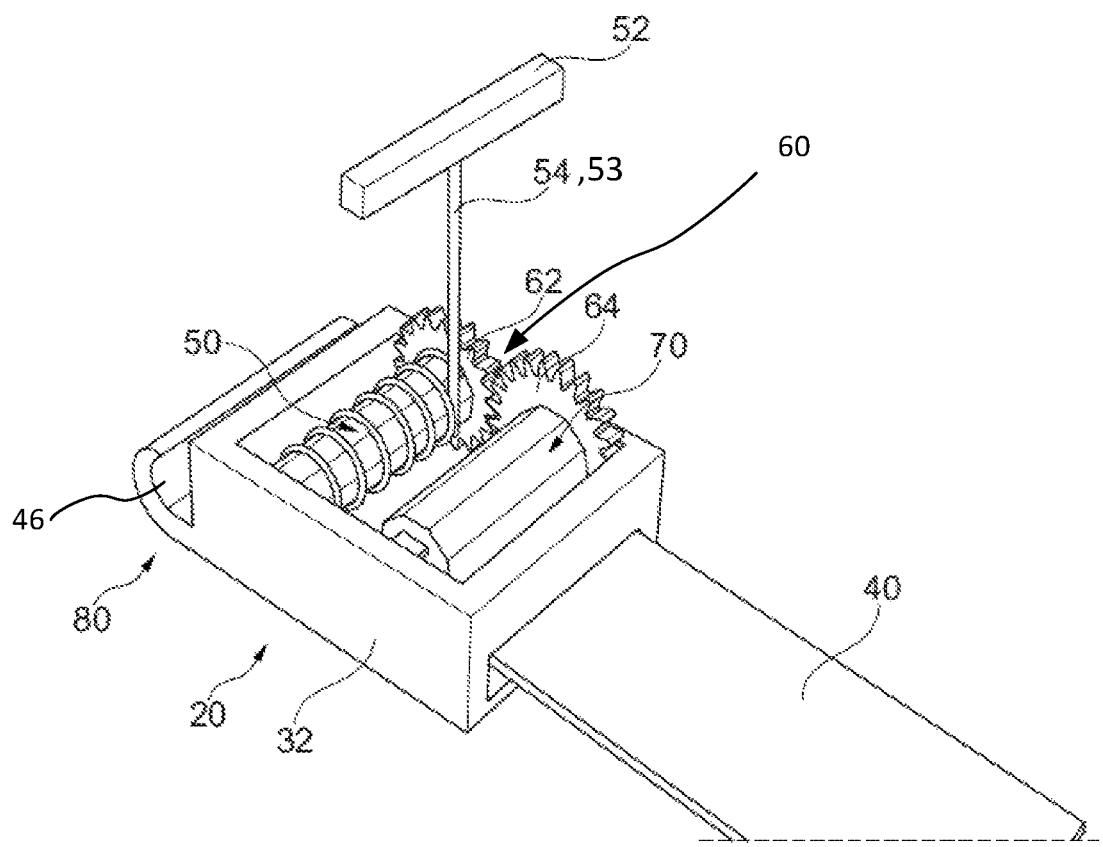
FIG. 1 shows schematically a perspective view of a tensioning device according to a first embodiment of the invention.

The following description of the exemplary embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to various forms of tightening devices used in connection with a tourniquet. It should be appreciated, however, that the referenced tightening devices and systems are also applicable and suitable for use in respect to any other type of tourniquet and applications apart from use in the field. Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment.

By the term limb in accordance with the present invention is to be understood an extremity of a human or animal such as a finger, hand, foot, leg, arm, also including parts of extremities.

The use of clockwise or counter clockwise in the description of the invention is only for the purpose of illustrating a rotational direction and the invention. It is not meant as limiting the invention to only relating to the specified direction of rotation of the component. The direction of rotation of the rotating components may be arranged differently without departing from the scope of the invention.

| Number | Description |
| --- | --- |
| 10 | Tourniquet |
| 20 | Tension adjustment device, tensioning device |
| 32 | Base/Housing |
| 34 | Cover |
| 36 | Screw fasteners |
| 40 | Strap |
| 42 | First end of the strap |
| 44 | Second end of the strap |
| 46 | Fastening means for second end of strap |
| 50 | Reel/spring loaded recoil cord reel |
| 52 | Handle |
| 53 | Rotation generating means |
| 54 | Pull-cord |
| 60 | Coupling means |
| 62 | First gear wheel |
| 64 | Second gear wheel |
| 66 | Third gear wheel |
| 70 | Arbor |
| 71 | Groove |
| 72 | First spacer |
| 74 | Second spacer |
| 75 | Inner cylinder |
| 77 | Ball |
| 78 | Recess in inner cylinder |
| 79 | Spring |
| 80 | Quick lock hook |
| 82 | Lock cylinder |
| 84 | Locking ring |
| 90 | Lock wheel |
| 92 | Spring loaded locking arm |
| 100 | First holding bracket |
| 102 | Second holding bracket |
| 110 | Recess |
| 120 | Release pin |
| 122 | Ring |
| 130 | Push pin |
| 132 | Cone shaped section |

The invention relates to a novel tourniquet, where tightening of the tourniquet is performed by linear motion by pulling a pull-cord. The tourniquet comprises a tensioning device and a strap. The first end of the strap is coupled to the tensioning device. The second end of the strap is wrapped around a limb and also fixed to the tensioning device. The tightening of the tourniquet is achieved by pulling the pull-cord. Linear motion by the pull-cord is translated into winding up the strap inside the tensioning device, and thereby tightening the tourniquet. Preferably, the tourniquet according to the present invention may further comprise a release mechanism that provides possibility to readjust or release the tightening of the tourniquet. Furthermore, it may comprise elements suitable to limit the maximum level of possible tightening.

FIG. 1 shows a first exemplary embodiment of a tensioning device 20 according to the invention. In FIG. 1 a base or housing 32 and a section of a strap 40 are shown. The strap 40 is fixed with a first end (not shown) to an arbor 70 mounted inside said base. In operation said strap 40 is tightened in a loop around an injured limb and fixed with the other (second) end (not shown) of the strap 40 to the other side of the base (not shown) e.g. by a quick lock hook 80. For the purpose of describing the invention the tensioning device 20 is shown without a cover. The base 32 provides support for the working mechanics for the tensioning device 20. A pull-cord recoil reel 50, where the pull-cord 54 is rolled up on the reel 50, is located inside the base 32. The reel 50 is internally coupled to the base 32 and may rotate around its longitudinal axis. A first gear wheel 62 is provided at an end of the reel 50. An arbor 70, whereto said first end 42 of the strap 40 is affixed and on which the strap 40 can be winded up during the tensioning procedure, is located inside the base 32 and can rotate around its longitudinal axis. The arbor 70 and the reel 50 are arranged in parallel along their longitudinal axis. A second gear wheel 64 is provided on the arbor 70. The first gear wheel 62 and the second gear wheel 64 are arranged in such a way that they mesh with each other and that their rotational axis is parallel for transfer of the rotational movement from the pull-cord activated reel 50 to the arbor 70 with the affixed strap 40. Thus, the gear wheel arrangement is such that rotations of the reel 50 are translated to rotations of the arbor 70 via the gear wheels 62, 64 provided on each of the rotatable reel 50 and arbor 70. The strap 40 is secured to the arbor 70 and clockwise rotations of the arbor 70 will wind the strap 40 up on the arbor 70. The first end 42 of the strap 40 may be secured to the arbor 70 by gluing, welding, stitching or similar. The first gear wheel 62 and the second gear wheel 64 typically have a conversion ratio of 3:1, where three complete rotations of the first gear wheel 62 are translated to one complete rotation of the second gear wheel 64. Such a conversion ratio will result in three times more tightening force applied to the strap for constriction than the linear force applied by pulling the pull-cord. Thereby an easier tightening of the tourniquet is achieved resulting in a particularly efficient constriction to stop venous and arterial blood circulation to an extremity.

In the disclosed tourniquets according to the present invention, the translation ratio from the first gear wheel 62 to the second gear wheel 64 may be chosen such that one rotation of the first gear wheel results in one or more rotations of the second gear wheel, preferably a ratio of 1:3. This is preferred in cases, where it would be advantageous to provide more rapid tightening of the tourniquet. In other embodiments of the tourniquet the translation ratio from the first gear wheel 62 to the second gear wheel 64 may be chosen such that one rotation of the first gear wheel results in one or more rotations of the second gear wheel, preferably at a ratio of 3:1. The advantage of this ratio is that less pull force is needed for tightening of the tourniquet.

The length of the pull-cord in the disclosed tourniquets according to the present invention is typically chosen in such a way that it can easily be operated single handed e.g. if the user is the injured person himself/herself. The pull-cord can typically have a length of 20 cm to 60 cm to be pulled using only one arm. The pull-cord may be shorter than 20 cm to allow a smaller dimension of the pull-cord reel. The pull-cord may be longer than 60 cm to allow an operator to apply more force to the arbor in a single movement. The pull cord handle may be configured for operation by one hand and/or two hands.

A quick lock hook 80 for attachment of the second end of the strap 40 is shown in FIG. 1. A corresponding quick lock hook (not shown) is provided on the free (second) end 44 of the strap. A quick lock assembly is formed when the two quick lock hooks engage with each other for fastening the free end of the strap to the base.

In another embodiment the quick lock hook 80 for attachment of the second end of the strap 40 may be shaped to correspond to the second end of the strap. The corresponding end of the strap may be molded in such a way that it slides sideways into the quick look hook and fixes the second end of the strap in the quick lock hook 80.

The tourniquet shown in FIG. 1 is preferably packaged in a disposable bag for protection and storage. Use of the tourniquet is performed by placing the tensioning device 20 on a limb (not shown) or an extremity above the bleeding wound. The strap 40 is wrapped around the wounded limb and the second free end of the strap 40 is secured to the quick lock hook 80. The quick lock assembly may provide some means for "gross" cinching tension of the tourniquet. The subsequent tightening of the tourniquet for constricting of the blood circulation is achieved by an operator pulling the handle 52 of the pull cord 54. The thereby achieved linear motion of the pull cord 54 will translate to linear tension of the strap 40 around the limb when the arbor 70 rotates.

The gear wheel arrangement 62, 64 may additionally comprise rotation locking means (not shown) to restrict unwinding of the strap 40 wrapped up on the arbor 70. These rotation locking means may be locking arms, frictions brakes, or similar means that prevent undesired unwinding of the strap 40. Alternatively, locking means for locking the rotational movement of the reel 50 and/or the arbor 70 may be provided directly on the reel 50 and/or the arbor 70.

In other embodiments the gear wheel arrangement may comprise additional intermediate gear wheels. Rotations of the first gear wheel 62 may be translated to rotations of the second gear 64 wheel via one or more intermediate gear wheels. An advantage with additional gear wheels is to allow a longer distance between the recoil reel 50 and the arbor 70 as well as a high translation of rotational movements.

In other embodiments the arbor 70 may have a slot where the free end of the first end of the strap can be entered through. This will give the possibility to apply gross cinching to the limb by the strap 40 before the rotation of the arbor 70 further tightens the tourniquet 10.

Figure 2:
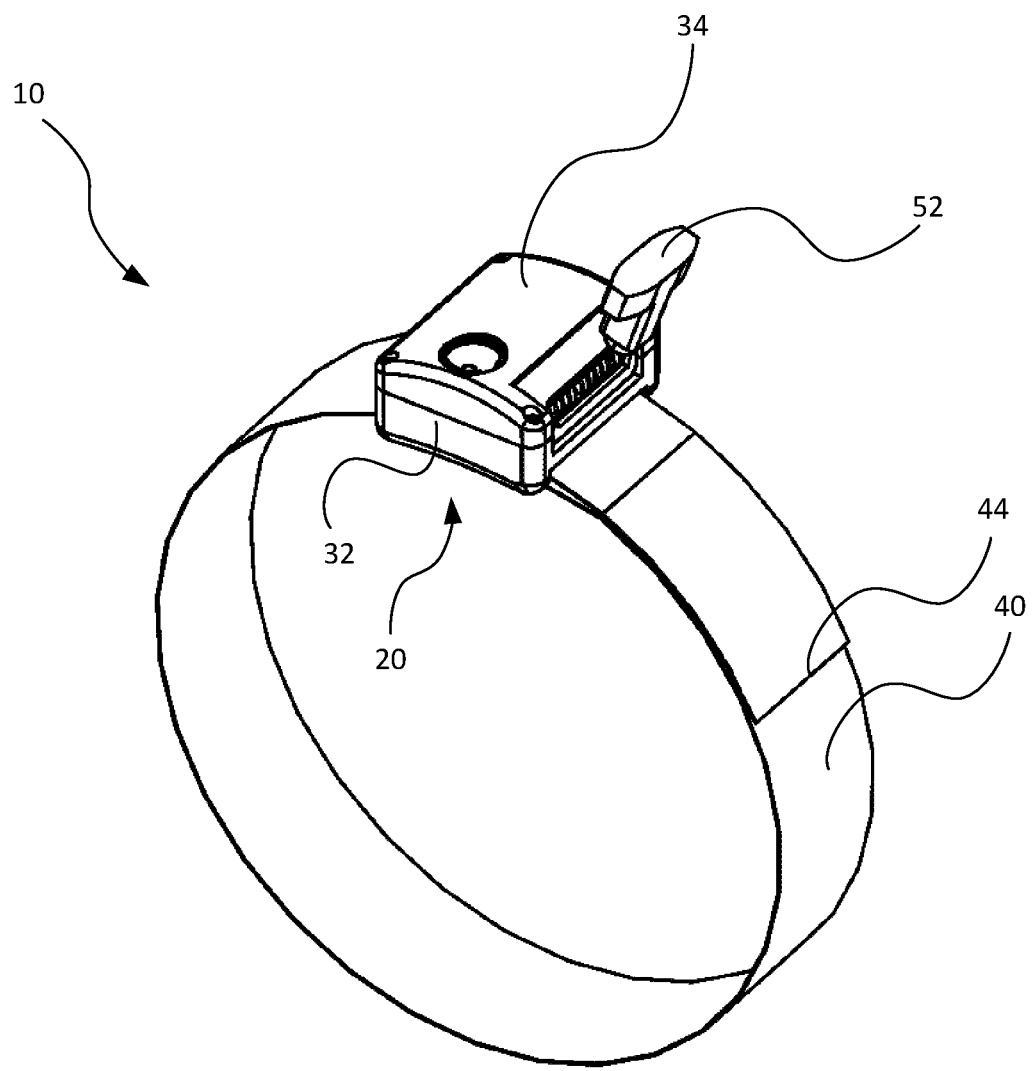
FIG. 2 shows schematically a perspective view of a tourniquet of a second embodiment according to the present invention indicating an assembled tourniquet.

A second embodiment of a tourniquet 10 according to the invention is shown in FIG. 2. As described above for the first embodiment, the tourniquet 10 comprises a strap 40 to be circumferentially arranged around an injured limb (not shown) in order to stop the flow of blood when constricted. The tourniquet 10 is designed to prevent blood loss in a patient's limb through the application of pressure to constrict the severed blood vessel. The tourniquet 10 further comprises a tension adjustment device 20 and mechanism which is coupled to the strap 40 on each side for constricting of said strap 40 after being placed around said limb. The tension adjustment device and mechanism 20 is typically placed inside a housing/base 32.

Preferably, the strap 40 is fabricated from a lightweight and strong material, such as polyester or nylon webbing, with a typical width of 3 cm to 10 cm, and more preferably 5 cm width. Other material may also be employed, such as strong or reinforced synthetic fibers, textiles (woven or non-woven), leather, and cloth. In the context of the invention strong material should be interpreted as a material that is suitable to sustain the tension needed to constrict bleeding from a wound. The tourniquet 10 is preferably designed to provide initial "gross" tension by cinching the strap 40 and finely adjusting the tension by manipulating the tension adjustment mechanism by means of the tension adjustment device 20.

Still referring to FIG. 2, the strap 40 has a first end (not shown) and a second end 44. The first end 42 is coupled to the tension mechanism inside the base/housing 32. The tourniquet is applied to a limb by wrapping the strap 40 around the patient's limb and securing and affixing the second end 44 of the strap 40 to the housing 32. The second end 44 is preferably detachable from said housing 32 and can be secured to the housing 32 by fastening means such as a quick attach mechanism e.g. as described for FIG. 1. A quick attach mechanism as described below has the advantage that the strap can be fastened and pre-tightened in a fast expedient and efficient one-step procedure. The feature of a detachable second end 44 of the strap 40 facilitates the positioning of the strap 40 around the injured limb as well as its removal. It is thus a more gentle procedure for the patient. Moreover, it allows a flexible use of the tourniquet 10 for different types of limbs having different circumferences, since the length of the strap 40 can easily and efficiently be adjusted to the length afforded for embracing said limb. In an alternative less preferred embodiment (not shown), however, the strap 40 may be permanently fixed to the housing. In this case, the strap is pre-fixed in form of a loop and has to be drawn over the limb for positioning. In this case, the circumference of the loop should more or less correspond to the circumference of the limb in order to facilitate the later constriction of the strap or it should be provided with a suitable adjustment mechanism to adjust the size of the loop.

Figure 3:
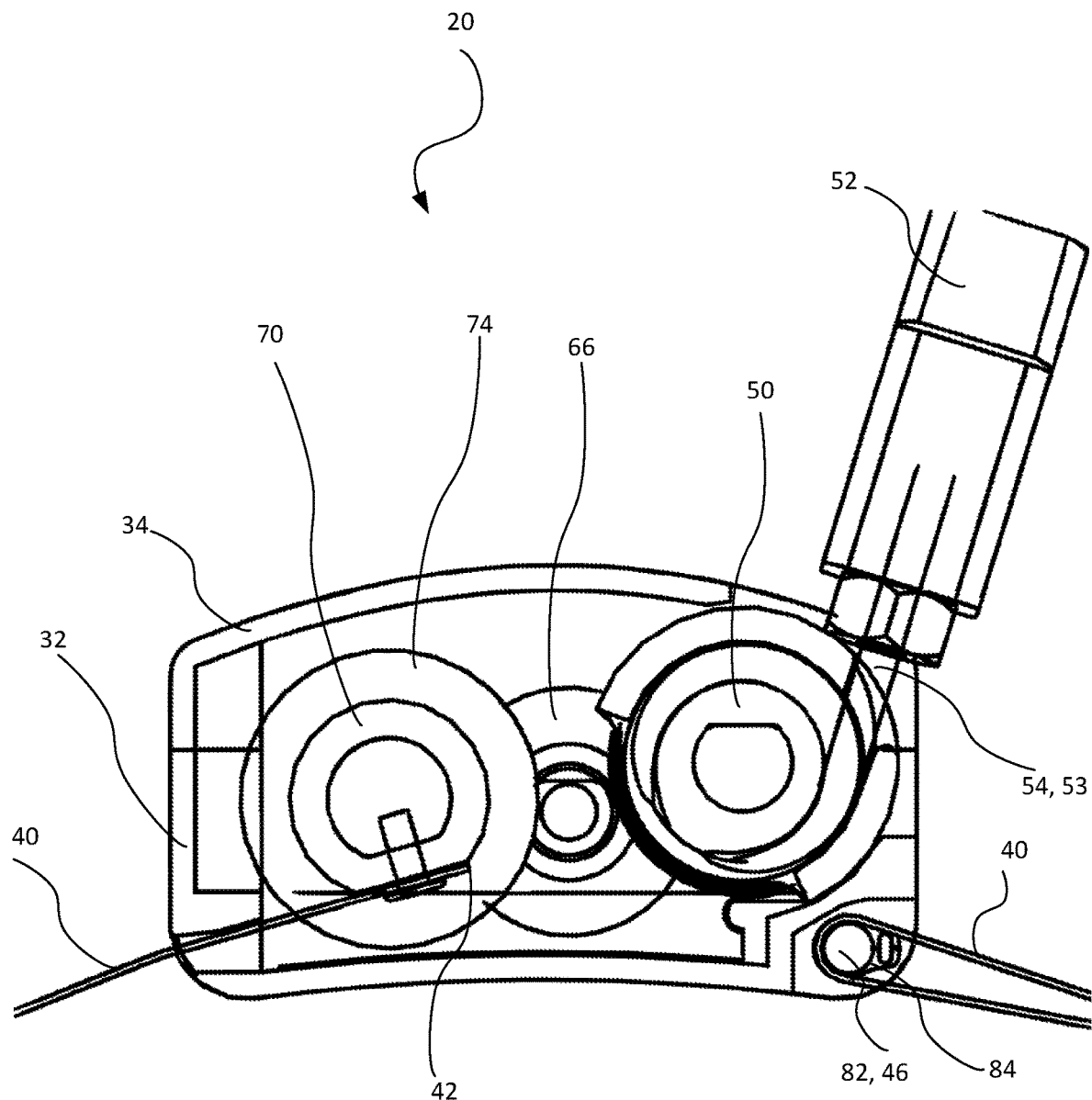
FIG. 3 shows schematically a cross section view from the side of the second embodiment according to FIG. 2.

A quick attach mechanism which can be used in tourniquets according to the present invention is typically a Velcro™ buckle lock. FIG. 3 shows a cross sectional view of the tensioning device 20, where the second end 44 of the strap 40 is entered through an opening and looped around a lock cylinder 82 forming a loop. The lock cylinder 82 has at least a locking ring 84 that will prevent the strap 40 from any sideways movement. The strap 40 preferably comprises a Velcro™ fastener at the second end 44 of the strap 40 as well as with a corresponding section of Velcro™ on another area of the strap 40. When the second end 44 of the strap 40 is looped around the lock cylinder 82 the end of the second end 44 of the strap 40 may be secured to said Velcro™ section on the strap 40.

The quick attach mechanism for a tourniquet according to the present invention can also comprise a magnetic locking device. Such a magnetic locking device may comprise a first member that is coupled to the housing 32 and a second member that is attached or coupled to the second end 44 of the strap 40. The first and the second member can engage with each other to securely fasten the second end of the strap to the housing 32. The first member and the second member comprise at least one magnet and the first and second member are held together by magnetic attraction between the magnets. The first member and the second member may be releasable locked to each other and are used to connect the second end of the strap 40 to the housing 32. The second member may be provided with adjustment means for the initial "gross" tension by cinching the strap around the limb.

Other types of quick attach mechanism may alternatively be applied in any of the disclosed tourniquets according to the present invention, including, but not limited to, hook and loop, a seatbelt-type attachments, clips fasteners or similar. The quick attachment means are used to quickly and reliably secure the second end of the strap 40 to the housing.

The quick attach mechanism may provide adjustment means for the initial "gross" tension by cinching the strap around the limb. The initial gross tensioning is performed by tightening the strap through the self locking loop. It is advantageous to perform initial gross tensioning to reduce the strap that needs to be winded up inside the tensioning device.

Other types of gross cinching devices or techniques may alternatively be applied, including, but not limited to, hook and loop fastening material, a seatbelt-type clamping assembly, two-part adhesives, zip ties, Velcro™, etc.

The final adjustment of the tension is done by manipulating the tension adjustment mechanism. The manipulation of the tension mechanism is performed by pulling a handle 52 coupled to a pull-cord 54. Linear motion applied to the pull-cord 54 is thereby translated into linear motion applied to the strap 40 via the tensioning device 20. Pulling the handle 52 of the pull-cord 54 will increase the tension applied by the strap 40 wrapped around the limb.

In other embodiments the strap 40 may comprise several band sections, where at least a first section is coupled to the tension adjustment mechanism and there is provided means for coupling the additional sections together forming a continuous strap to be arranged around the limb. The strap 40 is then attached to a quick attach mechanism on the tension adjustment device 20. The strap 40 may comprise an adjustment means for adjusting the length of the strap 40. The adjustment means for shortening the strap can e.g. be double D-rings, Velcro™, loop-and-hook, and the like.

Figure 4:
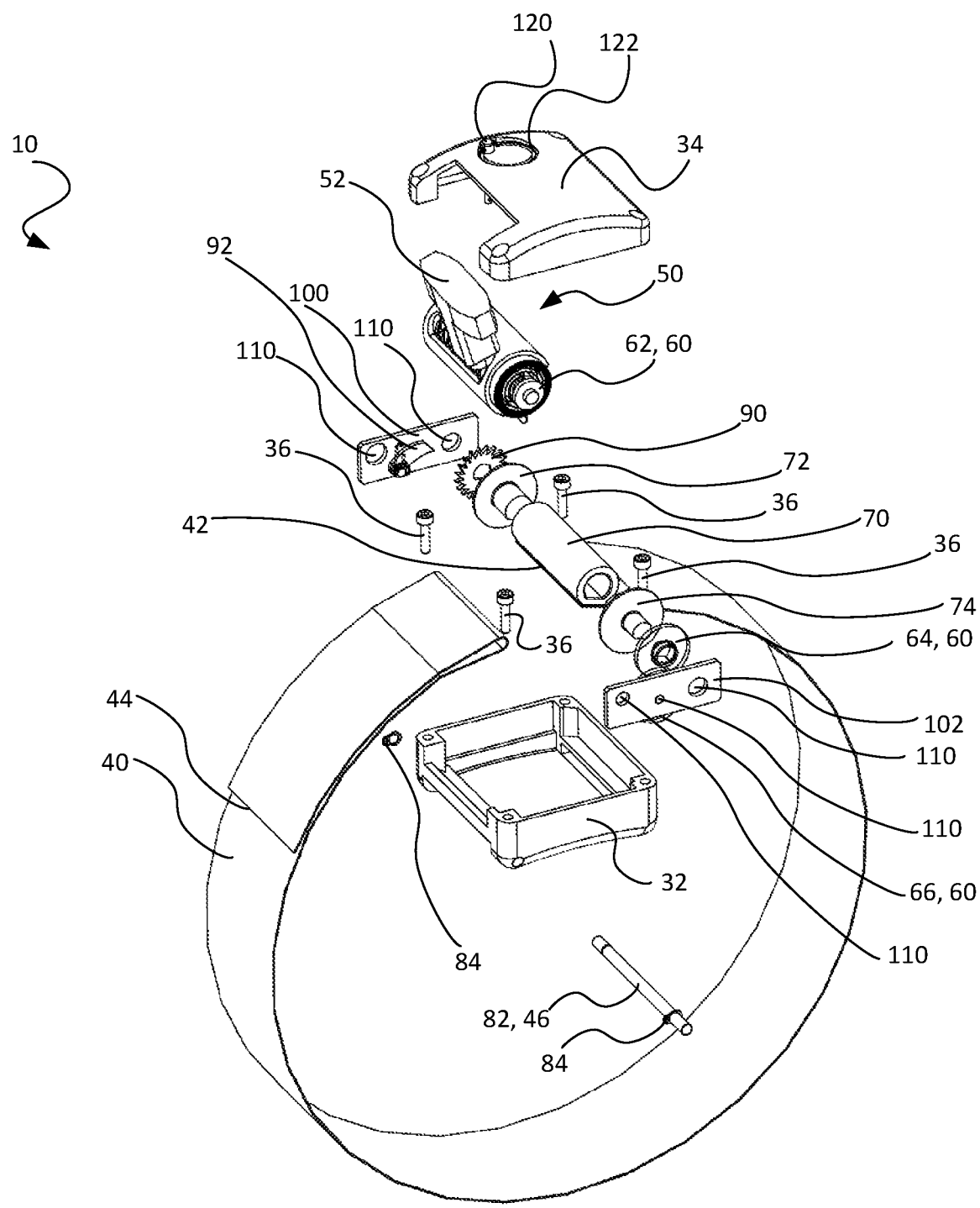
FIG. 4 shows schematically an exploded view in perspective of the second embodiment according to FIG. 2.

FIG. 4 shows an exploded view of the second exemplary embodiment of a tourniquet 10 according to the present invention. The shown tourniquet 10 comprises a strap 40 and a tensioning device 20. The tensioning device 20 comprises a housing 32 which contains the working components of the tensioning device 20. The housing is in form of a base 32 and has a corresponding cover 34. The base 32 and the cover 34 mate with one another, and are suitably attached, for example, by screw fasteners 36, to encase the working components of the tensioning mechanism. The attachment of the base 32 and the cover 34 may also be based on other suitable techniques such as bonding with adhesive, bonding by solvent, heat staking/welding, gluing, ultrasonic welding, and mechanical snap fasteners etc. The housing may be fabricated from lightweight, strong material, such as plastic, a lightweight metal and/or metal alloy, ceramics, or composites, also including combinations thereof.

Still referring to FIG. 4, the tensioning mechanism includes a spring loaded recoil reel 50. The spring loaded recoil reel 50 comprises a handle 52 attached to a second end of a pull-cord (not shown). The first end of the pull-cord is attached to the recoil reel 50 in form of a cylinder. The pull-cord is preferably rolled up on the recoil reel cylinder prior to use. The recoil reel 50 preferably further comprises a rewind spring to rewind the pull-cord up on the reel. The rewind spring may be a flat spiral spring where the inner end is coupled to the cylinder and the outer end is secured to the base. When pulling the pull-cord, by means of the handle 52, linear motion of the pull-cord is translated to rotation of the recoil reel with the winded cord and attached second end of the cord. The linear motion of the pull-cord will tension the rewind spring. When the handle is released the rewind spring will rewind the pull-cord up on the reel 50. The rotation of the reel is further translated via a clutch mechanism (not shown in FIG. 4) to rotation of a first gear wheel 62, which is connected coaxially via the clutch mechanism to the recoil reel 50. A person skilled in the art would know how to construct a clutch mechanism that temporarily disengages the reel from the first gear wheel when the pull-cord is rewinded up on the reel and this is therefore not explained in more detail. The recoil reel to be used in the tourniquets according to the present invention may be fabricated in any suitable and lightweight material like plastic or metal or a combination of the two. The pull-cord is preferably made in a flexible, water resistant material which is able to sustain the forces acting upon it when pulling the pull-cord; examples are nylon, or metal wire.

The rewind functionality of the pull-cord may well be achieved by a suitable arrangement of a rubber band or other means coupled to the reel 50. After releasing the pull-cord, the pull-cord will rewind on to the reel.

The tensioning mechanism further comprises means for linearly shortening the strap 40. As shown in FIG. 4, the tensioning mechanism is in form of an arbor 70. The first end 42 of the strap 40 is secured to the arbor 70. The arbor 70 has a first end and a second end along its longitudinal axis. A lock wheel 90 and a first spacer element 72 are coupled to the first end of the arbor 70. Similarly, a second spacer element 74 and a second gear wheel 64 are coupled to the second end of the arbor 70. The spacer elements 72, 74, the arbor 70, the lock wheel 90, and the second gear wheel 64 together form a unit that rotates together. The lock wheel 90 has the function to prevent unwinding of the arbor 70.

Preferably, the first end of the strap 42 is secured to the arbor 70 by gluing, but may be affixed by stitching, welding or other suitable ways to secure a strap end to an object. The arbor 70 in the disclosed tensioning devices according to the present invention can be fabricated from any suitable material like plastic, or metal.

Preferably, the spacer elements 72, 74, the arbor 70, the lock wheel 90, and the second gear wheel 64 are separate parts, but may also be manufactured as a integral piece in the same material. Said elements may be fabricated from any suitable material like plastic, or metal.

A first and a second holding bracket 100,102 are provided to fix the mechanic workings inside to the housing. The working mechanics comprise the arbor 70 with the spacer elements 72, 74, the lock wheel 90 and second gear wheel 64, the recoil reel 50 with the first gear wheel 62, and a third gear wheel 66. The holding brackets 100, 102 are provided with recesses 110 for accommodating protrusions on the longitudinal axis of the working mechanics. The holding brackets 100, 102 fix the arbor 70 and the recoil reel 50 in such a way that the arbor 70 and the recoil reel 50 are parallel. The second holding bracket is provided with recesses for fixing the first, second, and third gear wheel 62, 64, 66. The gear wheels 62, 64, 66 together form a gear system.

The gear system is adapted to translate the force applied by pulling the pull-cord (not shown) of the recoil reel 70 to linear motion applied to the strap 40. In the gear system the first gear wheel 62 is rotated by the linear motion of pulling the pull-cord of the recoil reel 70. The first gear wheel 62 meshes with the third gear wheel 66. The third gear wheel 66 meshes with the second gear wheel 64. Rotations of the first gear wheel 62 are transferred to rotations of the second gear wheel 64, via the third gear wheel 66, at a ratio of 3:1. It is appreciated that the number of gear wheels may vary and can e.g. be more than three in other embodiments.

Figure 5:
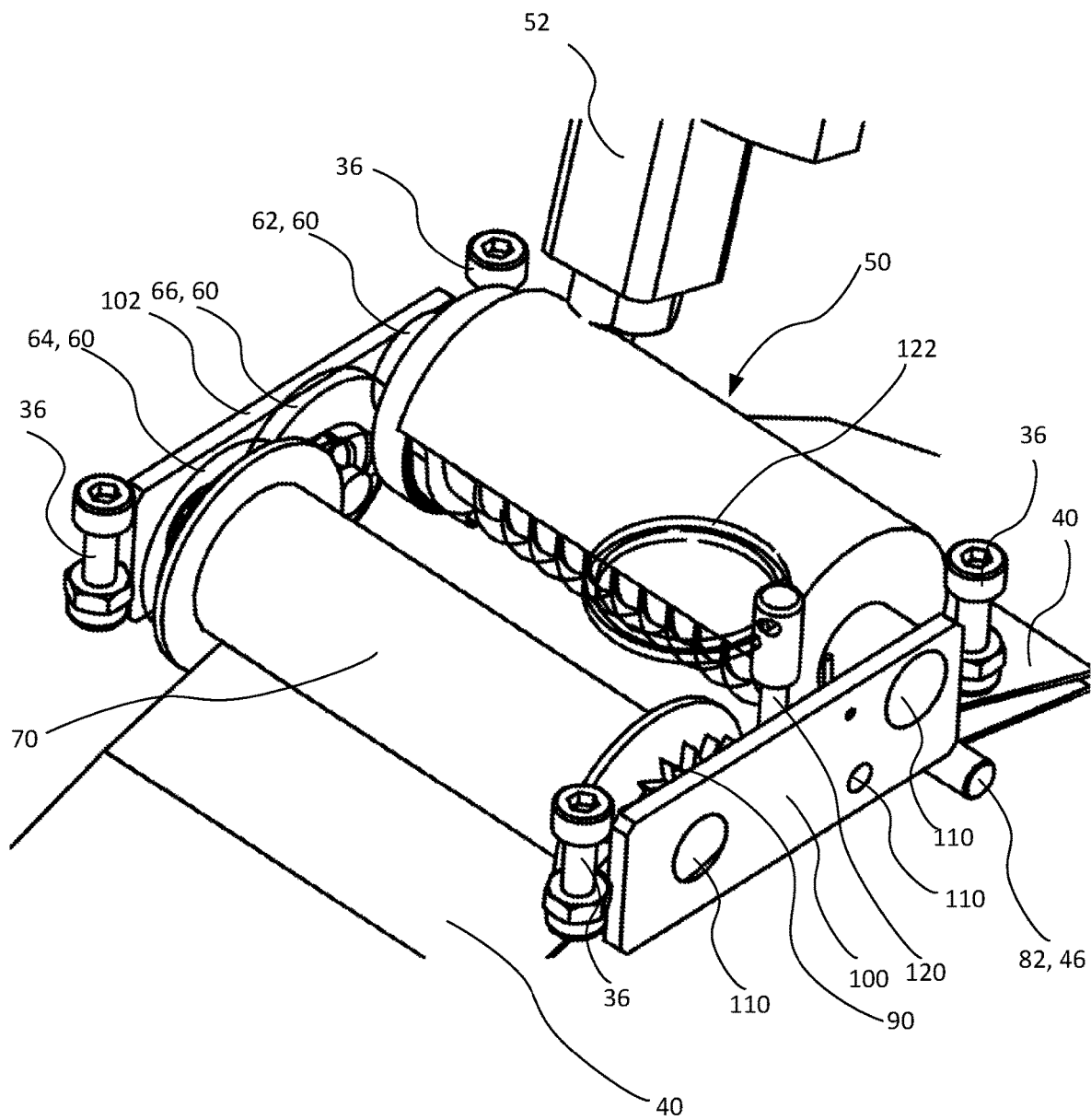
FIG. 5 shows schematically a perspective view of the mechanical workings of the second embodiment according to FIG. 2.

Referring to FIG. 5 the working mechanics are shown as fixed between the holding brackets 100, 102. The recesses 110 of the holding brackets 100,102 allow the arbor 70 and the recoil reel 50 to rotate around their longitudinal axis.

Referring to FIG. 4 the first holding bracket 100 further comprises a spring loaded locking arm 92. The locking arm 92 engages with the lock wheel 90 and stops counter clockwise rotations of the arbor 70. The locking arm 92 and the lock wheel 90 form a locking arrangement for stopping unwinding of the strap 40 that is winded on to the arbor 70 during tensioning of the tourniquet 10. The locking arrangement will allow rotations of the arbor for winding up the strap.

Preferably, the locking arrangement comprises the disclosed spring loaded locking arm 92 and the lock wheel 90. In other embodiments the locking arrangement may be designed using friction brakes or other means that prevents unwinding of the strap on the arbor.

The brackets and the gear wheels may be made of a suitable lightweight and robust material like metals, plastics, ceramics, or composites.

In the embodiment shown in FIG. 4, the recesses 110 are circular holes through the flat surface of the brackets. In other embodiments the recesses may be only small cavities in the surface.

In some embodiments the gear system may be designed with friction gears, belts, worm gears, or other means to translate the linear movement applied by pulling the pull-cord, via the recoil reel, to rotational movement applied to the arbor.

In some embodiments the gear system may have gear ratio chosen such that one rotation of the reel results in one or more rotations of the arbor, preferably a ratio of 1:3 or 1:2, to achieve more rapid tensioning of the tourniquet. It would in other embodiments be advantageous to have a gear ratio chosen such that one rotation of the reel results in less than one rotation of the arbor, preferably a ratio of 2:1 or 3:1. This requires less linear force to be applied by pulling the pull-cord during tensioning of the tourniquet.

In FIG. 4 a release mechanism suitable for manual activation by an operator, is provided through a second opening in the cover 34. The release mechanism comprises a release pin 120 that engages with the locking arm 92. In place the release pin 120 will force the locking arm 92 to stop all counter clockwise rotation of the arbor 70. Removing the release pin 120 will disengage the locking arm 92 from the lock wheel 90 with the result that the arbor 70 is free to rotate in a counter clockwise direction and release the tension of the strap 40. The release pin 120, as shown in FIG. 4, is accessible from the outside of the assembled housing. Coupled to the release pin 120 is a ring 122, where the ring 122 makes it easier to get hold of the release pin 120.

In some embodiments the release mechanism may be made in such a way that the arbor can be relocked, e.g. by a push button coupled to a spring loaded release pin that temporarily disengages the lock arm from the locking wheel.

During assembly of the tensioning mechanism, the arbor 70, the gear system 62, 64, 66, and the recoil reel 50 are held in place by the brackets 100,102 when fitted inside the base 32 and when the cover 34 is attached. The brackets 100, 102 are held in place by fitted slots in the base 32. The handle 52 of the recoil reel 50 will then be located externally to the housing. A schematically view of the mechanical workings of the second embodiment is shown in FIG. 5.

Figure 6:
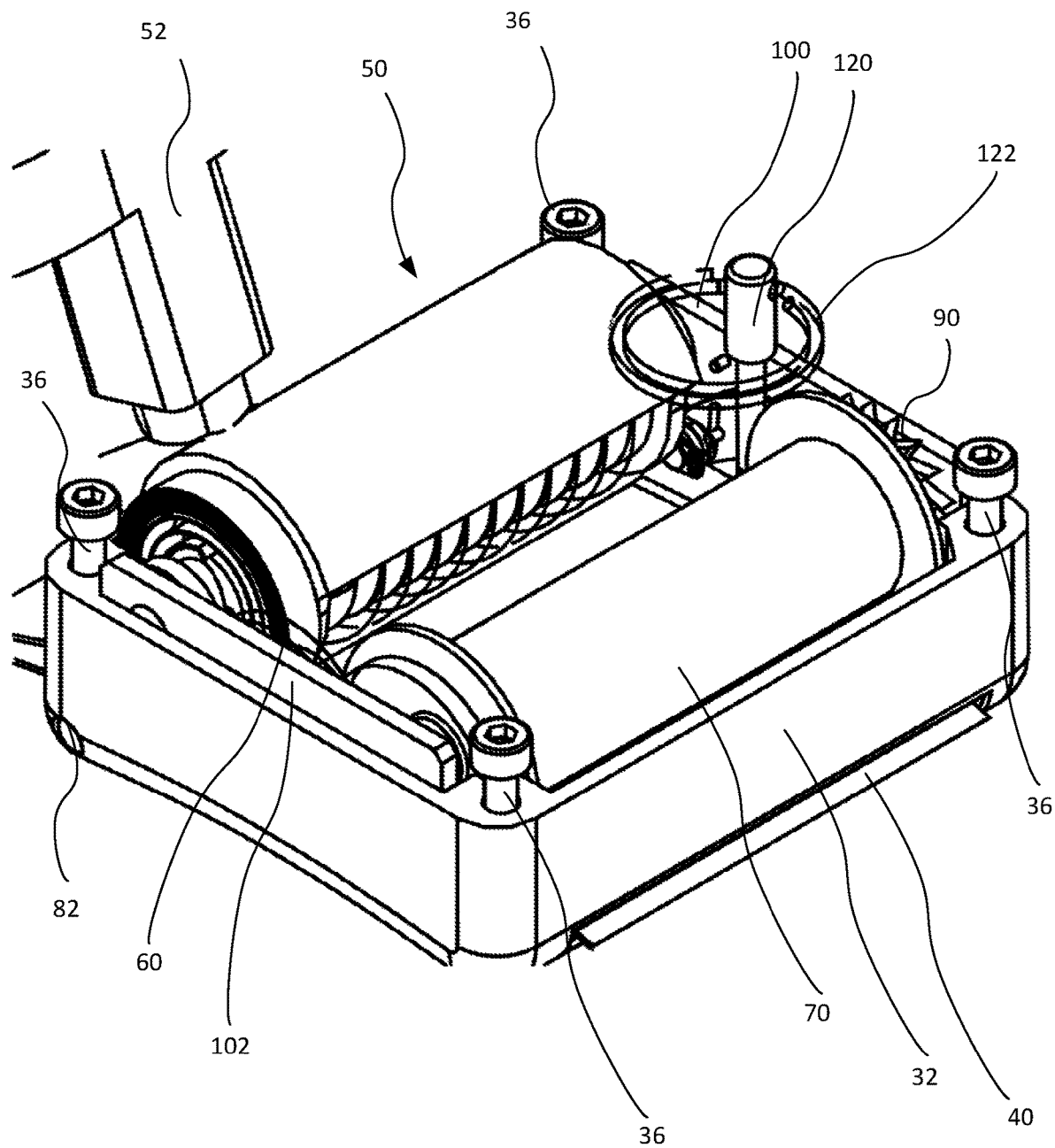
FIG. 6 shows schematically a perspective view of the housing of the second embodiment according to FIG. 2 without cover.

In FIG. 6 is shown a view of the housing of the second embodiment where the cover 34 has been removed. The brackets 102, 100 fix the arbor 70 and the recoil reel 50 inside the base 32. The strap 40 is entered through an opening in the base 32 and fixed to the arbor 70. Linear force applied by pulling the handle 52 is transferred to the arbor 70 via the gear wheel system and the strap 40 is winded up on the arbor 70.

Figure 7:
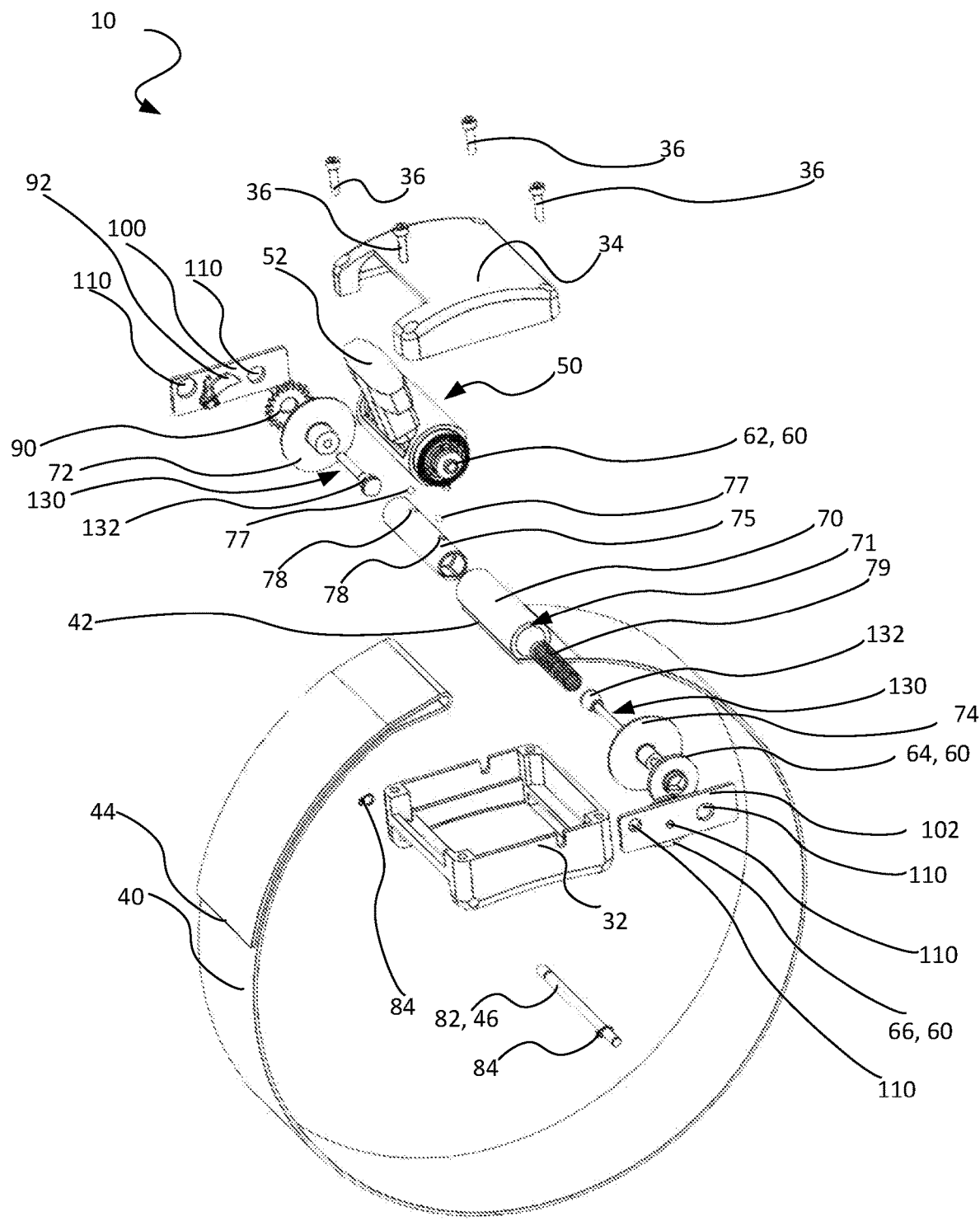
FIG. 7 shows schematically an exploded view in perspective from the side of a third embodiment.

In FIG. 7 is shown an exploded view of a third exemplary embodiment of a tourniquet according to the present invention. The third exemplary embodiment of the tourniquet 10 corresponds to the second exemplary embodiment apart from an alternative release mechanism for the arbor 70. Referring to FIG. 7, the release mechanism for the arbor 70 is a spring loaded ball locking mechanism. The spring loaded ball locking mechanism in addition to the arbor 70 comprises an inner cylinder 75 with two circular recesses 78, two balls 77, two push pins 130 and a spring 79. The inner cylinder 75 is dimensioned to fit inside the arbor 70. Inside the arbor 70 there is at least one longitudinal groove 71, suitable in size to engage with the two balls 77. The circular recesses 78 are on a common longitudinal axis of the inner cylinder 75 and are dimensioned such that whole or parts of the balls 77 can pass through. The two push pins 130 are provided with a cone shaped section 132 at a first end of each pin 130 facing towards the center of the arbor. Assembling of the arbor 70 with the spring loaded ball locking mechanism is performed by placing the spring 79 inside the inner cylinder 75, the two push pins 130 are placed inside the inner cylinder facing with their coned end part 132 towards the central spring 79. One ball 77 is placed in each of the recesses 78 and is resting against the cone shaped section 132 of the push pins 130 in each end of the spring 79. The inner cylinder 75 with the two balls 77, the spring 79 and the push pins 130 are placed inside the arbor 70. The ball 77 engages with the inner groove 71 of the arbor 70 and secures the inner cylinder 75 to the arbor 70 and the arbor 70 and the inner cylinder 75 rotate together. The tourniquet 10 is otherwise assembled and constructed in similar fashion as previously described for the second embodiment. The push pins 130 from the release mechanism protrude through the base 32 through recesses in the side walls of the base 32. Pushing the push pins 130 by an operator towards the center of the longitudinal axis of the arbor 70 will disengage the balls 77 from the groove 71 due to a reduced diameter of the cone of the push pins, when dislocated by pushing them inwardly towards the center of the arbor 70. Thereby, the balls 77 are released from their position and the arbor is unblocked. The arbor 70 can now rotate more or less freely and release the strap 40 that is winded around the arbor 70. When the push pins 130 are released, they will be pressed into their starting position by the now expanding spring 79. Thereby the cones 132 of the push pins 130 will press the balls through the recesses 78 of the inner cylinder 75 into the circumferential grooves 71 of the arbor 70 and the rotational movement of arbor will be locked and hindered again from further rotations and unwinding.

The push pins 130 are suitable to release and/or to adjust the tension/constriction when the tourniquet is tensioned around a limb. The third embodiment of the tourniquet 10 is otherwise operated and applied to a patient similar to other known tourniquets and as principally described above for the first and second embodiment. The described locking mechanism has the great advantage that it is easy to release the tourniquet e.g. for checking whether the bleeding has stopped or in cases where the constriction is too high and causes pain. The described mechanisms allow releasing, adjusting and reconstricting the tourniquet repeatedly without problems. Another advantage of the described release mechanism is that the tension in the spring 79 and angle of the cone shaped section 132 may be selected to disengage the balls 77 from the groove above a certain tensioning degree of the tourniquet. It is considered that a tourniquet tension of more than about 600 mm Hg may inflict permanent damage to tissue and nerves. In a preferred embodiment the spring tension and cone angle may be selected to prevent the tourniquet to be tightened above a certain threshold. In other circumstances there may be a need for the release mechanism to release at a higher level e.g. when the tourniquet is applied over clothes to make sure that the bleeding is properly stopped.

Figure 8:
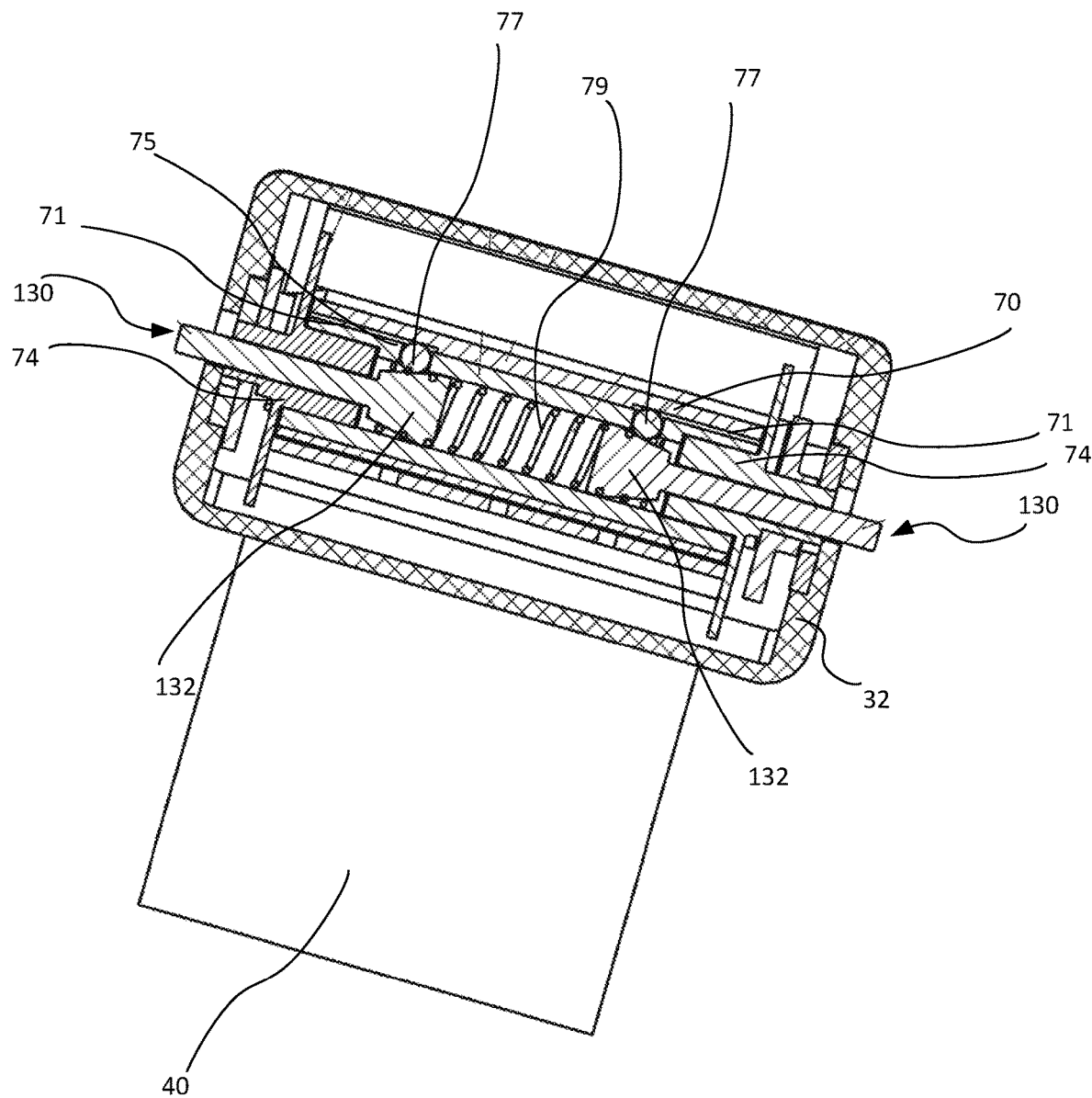
FIG. 8 shows a cross sectional view of the tension device of the third embodiment.

FIG. 8 shows a cross sectional view of the tension device of the third embodiment of the tourniquet 10. The housing 32 is surrounding the inner mechanics of the tensioning device. The spring 79 is placed inside the inner cylinder 75. The balls 77 are resting against the cone shaped section 132 of the pins 120 inside the inner cylinder 75. The inner cylinder 75 is inside the arbor 70. There is at least one longitudinal groove 71 inside the arbor 70 extending into the area where the balls contact the arbor 70 through the recesses in the inner cylinder 75. When the spring loaded ball locking mechanism is enabled, the balls 77 are pushed against a corresponding groove 71 and are locking the inner cylinder to the arbor 70. The balls 77 are pushed through a corresponding recess in the inner cylinder 75 as described above. When the spring loaded ball lock mechanism is enabled, the inner cylinder and the arbor are rotatable locked to each other. Pushing the pins 120 in the longitudinal direction of the inner cylinder the balls 77 will disengage the balls from the groove and let the arbor rotate freely. The inner cylinder 75 is coupled directly or via gear wheels to the locking wheel, whereby undesired rotations of the inner cylinder are prevented. When pulling the pull cord, the linear movement of the pull cord is transformed into rotations of the reel. Rotation of the reel is then transmitted via a coupling comprising gear wheels 62, 64 to the inner cylinder 75 whereby rotating the arbor 70 and winding up the strap 40. As long as the spring load ball locking mechanism is enabled the inner cylinder 75 and arbor 70 rotate together. The locking wheel 90 is connected to the inner cylinder 75 and will prevent unwinding of the strap winded up on the arbor 70. When the spring loaded ball locking mechanism is disengaged by pressing the pins 130, the arbor may rotate and unwind the strap. The inner cylinder is, due to its coupling to the locking wheel, prevented from rotating in the direction that unwinds the strap.

This simple and efficient release mechanism has the advantage that the tension of the tourniquet may be released and reapplied easily. The release mechanism relocks the rotations of the arbor when the push pins are released. It is common to rapidly apply and tighten a tourniquet around bleeding limbs as a first treatment step to save life. After the tourniquet has been applied, one will typically reassess within certain intervals whether a constriction is further needed by releasing or adjusting the tourniquet.

In other embodiments of the invention, not shown, there may be more than two balls in the release mechanism to accommodate more fine grained control of the release mechanism.

In other embodiments (not shown) the release mechanism may comprise one push pin to simplify manufacturing or make the system easier to operate.

The release mechanism of the invention may in other embodiments be provided with other means suitable to achieve comparable effects such as releasable friction locks or other means that may let the arbor temporarily unwind the strap.

The arbor may be coupled to other means suitable to prevent undesired unwinding of the strap e.g. locking arms, brakes, one way rotational locks or similar. In some embodiments with release mechanisms there may be means to prevent undesired rotations of the arbor during tightening of the tourniquet like locking wheels, brakes, or one-way rotational locks.

In another embodiment of the invention, not shown, the tourniquet comprises a tandem formation with two arbors for simultaneous winding up the first and the second end of the strap arranged around a limb. In this embodiment, the tourniquet comprises a pull cord reel as described for any of the preceding figures, a first and a second arbor and an appropriate gearing mechanism transferring the rotational movement obtained by activating the pull cord to both arbors. A housing provides support for the mechanics. Thereby, the housing has two openings allowing the strap to be winded up simultaneously by two arbors. The first end of the strap may be secured to the first arbor and the second end of the strap may be secured to the second arbor. A gear mechanism is provided which is mechanically coupled to the pull cord reel, the first arbor and the second arbor. A pull cord is winded up on the pull cord reel. The first end of the pull cord is secured to the reel and the second end of the pull cord is free to be pulled. Upon pulling the second end of the pull cord the reel rotates. Rotations of the reel are translated to rotations of the two arbors. In use the first end of the strap is secured to the first arbor. The second end is wrapped around the wounded limb. Thereafter the second end is secured to the second arbor. The strap and the arbor may be provided with means for shortening to provide gross tension by cinching around the limb. Pulling the pull cord will further provided tension around the limb by winding the strap on to the first and second arbor. The transmission of the rotation of the reel may be translated as equal rotations on both the arbors. Rotations of the reel may alternatively be translated at different ratios to the first and second arbor. This is advantageous in allowing different sizing of the arbors, in particular when available space differs inside the housing around each of the arbors.

In another simpler embodiment of the invention, not shown, the tourniquet comprises a combined arbor and pull-cord reel. In this embodiment the combined arbor and pull-cord reel are connected via a coupling in the longitudinal axis of the arbor and pull-cord reel. A housing provides support for the mechanics. Thereby, the housing has an opening allowing the strap to be winded up by the arbor. The first end of the strap is secured to the arbor. The second end of the strap may be secured to the housing. A pull-cord is winded up on the pull-cord reel. The first end of a pull-cord is secured to the reel and the second end of the pull-cord is free to be pulled. Upon pulling the second end of the pull-cord the reel rotates. Rotations of the pull-cord reel are translated to rotations of the arbor via the direct coupling between the arbor and the pull-cord reel. In use the first end of the strap is secured to the arbor. The second end is wrapped around the wounded limb. Thereafter the second end is secured to the housing. The strap may be provided with means for shortening to provide gross tension by cinching of the limb. Pulling the pull-cord will further provide tension around the limb by winding the strap on to the arbor. The disadvantage of this simplified embodiment is that there is no translation by gear wheels between the rotating reel and the arbor which results in that the forces applied by pulling the pull-cord needed to constrict the tourniquet are much higher.

The coupling preferably comprises a clutch mechanism, as described in the preceding sections, allowing rewinding of the pull-cord on to the recoil reel. In less preferable embodiment the coupling is a direct connection where the arbor and the pull-cord reel share a common shaft. An advantage of a common shaft is to simplify manufacture of the tourniquet. In another less preferred embodiment, the coupling between the arbor and the pull-cord reel may be a combination of a clutch mechanism and/or gear wheels. Said arrangement of a clutch mechanism and/or gear wheel may be advantageous to allow rewinding of the pull-cord and/or different translation rate of rotations of the pull-cord reel to the arbor.

In the preceding embodiments the reel should be understood to have a longitudinal axis that may rotate upon pulling the attached pull-cord. Similarly the arbor should be understood to have a longitudinal axis that may rotate for winding up a strap. The coupling between the reel and the arbor may comprise elements from a list of gear systems, gear wheels, clutches, direct connections etc. An advantage of the coupling is to transfer rotations of the reel to rotations of the arbor. The reel and at least one arbor can be mounted parallel in the housing. In other embodiments the reel and arbor may be mounted non-parallel in the housing to allow an optimized sizing of the tensioning device.

In a particular preferred embodiment of the tourniquet, not shown, the rotation axis of the pull-cord reel is perpendicular to the rotation axis of the arbor. Pulling the pull-cord the rotations from the reel is translated to rotations of the arbor that wind up the strap on the arbor. The translation of the rotations of the pull-cord reel to the arbor may be performed by gear wheels or similar solutions known to the skilled person in the field. Preferably, the possibility to pull the pull-cord upwards away from the tightening mechanism and injured limb is maintained such as by a suitable guiding mechanism, a wheel or similar. Such an arrangement where the pull-cord reel is perpendicular to the arbor accommodates the possibility for a larger pull-cord reel and a greater length of the pull-cord and a simpler design of the rewind mechanism of the pull-cord reel.

In a more preferred embodiment of the tourniquet, not shown, the arbor is provided with a mechanism that allows for adjusting the initial constriction (gross cinching) of the tourniquet before the tightening of the tourniquet by pulling the pull cord by means of the first strap. The tensioning mechanism comprises the arbor for winding up the first end of the strap as described above. Instead of the first end of the strap being attached to the arbor, the free end of the first end of the strap can be passed through the arbor. The arbor may be a cylinder provided with a slot where the free end of the first end of the strap is passed through.

The arbor is in addition provided with a brake mechanism that prevents the strap from reverse movement through the arbor. In use of the tourniquet the strap is first wrapped around a limb and the second end of the strap is attached to the housing by using a quick lock mechanism. The free end of the first end is passed through the arbor and out of the housing. Pulling the free end of first end of the strap will further tighten the strap around the limb. The subsequent tightening is performed by pulling the handle of the pull cord reel. The pulling of the pull cord reel converts the linear movement of the pull cord to rotational movement of the arbor. The first end of the strap is then wound up on the arbor. Preferably, the first end of the strap is provided with a handle or similar that makes holding and pulling easy. The brake mechanism in the arbor is preferably made of three parallel cylinders forming a friction brake. The strap can be passed around the cylinders in a winding path which due to friction is preventing the strap from reverse movement through the arbor. When rotating the arbor, with theses cylinders, the first end of the strap is wound up on the arbor and the strap is tightened around the limb for better occlusion. The pull cord reel is preferably perpendicular to the rotation axis of the arbor to save space of the tensioning mechanism. The quick lock assembly is preferably a magnetic quick lock for securing the second end of the strap to the housing. In other embodiments of the tourniquet the arbor is a cylinder provided with a longitudinal opening where the free end of the first end of the strap is passed through. The opening in the arbor is provided with teeth or friction area preventing the strap from reverse movement. In some embodiments the tourniquet 10 is provided with padding between the base 32 and skin of the limb. The padding is provided to prevent damage to the limb and prevent pinching of the skin during tightening of the tourniquet. The padding may be made of rubber, foam, fabric or other material suitable to protect the limb from the hard surface of the base.

In some embodiments the tourniquet 10 is provided with a strap 40 made of a smart textile. The smart textile may indicate level of tension applied to a limb by the tourniquet. The smart textile may indicate tension or stretching in a certain direction by change of color, pattern, sounds or odor. This may be used to indicate to the operator that sufficient tightening of tourniquet is attained or that not sufficient tightening is not applied.

In case of an emergency where rapid occlusion of a bleeding limb is needed the described tourniquet 10 according to the present invention may be used. Preferably, the tourniquet 10 is wrapped in a container or bag such as a plastic bag that may easily be opened with one hand. The tourniquet 10 is unwrapped from the plastic bag. The tensioning device 20 with the first end of the strap 42 attached is placed on the limb/extremity above the bleeding wound. The free end of the strap 40 is thereafter wrapped around the limb above the bleeding wound. The free end of the strap 40 is fixed through a quick lock assembly 82, 84 to the housing of the tensioning device 20, preferably on the base 32 of the housing. The tourniquet is tensioned by cinching the strap 20 using the quick lock assembly 82, 84. The subsequent tightening of the tourniquet is performed by pulling the handle 52 of the pull-cord 54. The rewind functionality of the recoil reel 50 will allow several repetitions of the pulling the handle 52 of the pull-cord 54 and releasing the handle 54. The repetitions of the tightening procedure will be repeated until a sufficient tension is applied by the tourniquet to stop bleeding from the limb. The tourniquet 10 may be released by e.g. removing the release pin 120 by pulling the ring 122 as described for the second embodiment or by pushing the push pins 130 of the ball locking mechanism as described for the third embodiment.

The tourniquet of the present invention may also be adapted to apply direct pressure on a flesh wound. For example, the tourniquet may be used with a gauze pad to apply direct pressure on the wound. The tension or amount of pressure applied by the tourniquet may be rapidly applied by the tensioning mechanism.

The tourniquet of the present invention may be adapted for reuse. For example, the housing is adapted for being suitably sterilized and the strap may be replaced with a new sterile strap. It may also be possible to sterilize at least parts of the tourniquet to enable reuse of parts or the complete tourniquet.

It should be understood in the scope of the invention that the materials for the tourniquet are preferably made in materials that may be sterilized and/or that are aseptic.

The invention claimed is:

1. A tourniquet comprising:
    a strap having a first end and a second end for encircling a limb, and
    a tensioning device comprising
    a housing wherein the housing comprises:
        a first arbor for attaching and winding up the first end of the strap,
        a fastening means for affixing the second end of the strap to the housing,
        a rotation generating means for providing rotations for winding in the strap,
        a coupling for transferring of rotations from the rotation generating means to the first arbor, and
        a locking mechanism to prevent unwinding of the strap,
    wherein the rotation generating means comprises a pull-cord for providing rotations for winding in the strap along the first arbor.

2. A tourniquet according to claim 1, wherein the rotation generating means comprises a pull-cord reel including a mechanism for recoiling the pull-cord on the pull-cord reel.

3. A tourniquet according to claim 2, wherein the coupling comprises a gear system for translation of rotations from the pull-cord reel to the first arbor.

4. A tourniquet according to claim 3, wherein the translation ratio between the pull-cord reel and the first arbor is at least 2:1.

5. A tourniquet according to claim 2, wherein the tensioning device comprises a release system suitable for disengaging the pull-cord reel from the first arbor.

6. A tourniquet according to claim 2, wherein a rotation axis of the first arbor is perpendicular to a rotation axis of the pull-cord reel.

7. A tourniquet according to claim 1, wherein the locking mechanism is releasable for unwinding the first end of the strap.

8. A tourniquet according to claim 1, wherein the fastening means comprises a second arbor for winding up the second end of the strap whereby the second arbor is connected via another coupling to the rotation generating means.

9. A tourniquet according to claim 1, wherein the locking mechanism is configured to unlock above a certain level of tension applied to the limb.

10. A tourniquet according to claim 1, wherein the strap is made of a smart textile for indicating tension applied to the limb.

11. A tourniquet according to claim 1, wherein the tourniquet comprises a release mechanism for preventing the tourniquet being tensioned over a certain tensioning degree.

12. A tourniquet according to claim 1, wherein the rotation of the first arbor is controlled by a spring loaded ball lock mechanism.

13. A tourniquet according to claim 1, wherein the first arbor comprises an opening for passing a free end of the first end of the strap through the opening.

14. A tourniquet according to claim 1, wherein winding in the strap along the first arbor includes pulling the strap along a winding path defined at least in part by the first arbor.

15. A tourniquet comprising:
    a strap having a first end and a second end; and a tensioning device including:
- an arbor for rotating along the strap to increase tension in the strap,
- an attach mechanism configured to removably affix to the second end of the strap,
- a pull-cord and a pull-cord reel, the pull-cord being configured to provide rotations to the pull-cord reel;
- a coupling for transferring rotations from the pull-cord reel to the arbor, and
- a locking mechanism to prevent release of the strap.

16. The tourniquet of claim 15, wherein the arbor includes an opening and the strap passes through the opening.

17. The tourniquet of claim 15, wherein the coupling includes a gear system.

* * * * *